US 9,937,052 B2

(12) United States Patent
Abdou et al.

(10) Patent No.: US 9,937,052 B2
(45) Date of Patent: Apr. 10, 2018

(54) METHODS AND APPARATUS FOR IMPLANTING AN INTERBODY DEVICE

(71) Applicant: COGENT SPINE LLC, San Diego, CA (US)

(72) Inventors: Samy Abdou, San Diego, CA (US); Brian Bowman, Carlsbad, CA (US); Benjamin Arnold, San Diego, CA (US); Jude Paganelli, San Diego, CA (US)

(73) Assignee: Cogent Spine LLC, San Diego, CA (US)

( * ) Notice: Subject to any disclaimer, the term of this patent is extended or adjusted under 35 U.S.C. 154(b) by 1150 days.

(21) Appl. No.: 13/834,782

(22) Filed: Mar. 15, 2013

(65) Prior Publication Data

US 2014/0277486 A1   Sep. 18, 2014

(51) Int. Cl.
*A61F 2/02* (2006.01)
*A61F 2/44* (2006.01)
*A61F 2/46* (2006.01)
*A61F 2/30* (2006.01)

(52) U.S. Cl.
CPC .......... *A61F 2/4455* (2013.01); *A61F 2/4465* (2013.01); *A61F 2/4611* (2013.01); *A61F 2002/3008* (2013.01); *A61F 2002/30172* (2013.01); *A61F 2002/30471* (2013.01); *A61F 2002/30777* (2013.01); *A61F 2002/30904* (2013.01); *A61F 2002/448* (2013.01); *A61F 2002/4627* (2013.01)

(58) Field of Classification Search
CPC ............. A61B 17/1757; A61B 17/7074; A61F 2/4611; A61F 2002/448; A61F 2002/4485

USPC ...................... 623/17.11–17.16; 606/99, 100
See application file for complete search history.

(56) References Cited

U.S. PATENT DOCUMENTS

| | | | |
|---|---|---|---|
| 6,387,130 B1 | 5/2002 | Stone et al. | |
| 7,655,042 B2 | 2/2010 | Foley et al. | |
| 8,002,833 B2 | 8/2011 | Fabris Monterumici et al. | |
| 8,021,429 B2 | 9/2011 | Viker | |
| 8,025,697 B2 | 9/2011 | McClellan, III et al. | |
| 8,034,109 B2 | 10/2011 | Zwirkoski | |
| 2002/0183761 A1* | 12/2002 | Johnson ............... | A61B 17/025 606/90 |
| 2003/0023306 A1* | 1/2003 | Liu ......................... | A61F 2/447 623/17.11 |

(Continued)

FOREIGN PATENT DOCUMENTS

EP     1980222     *  4/2008  ........... A61F 2/4465

*Primary Examiner* — Matthew Lawson
(74) *Attorney, Agent, or Firm* — Gazdzinski & Associates, PC

(57) ABSTRACT

A delivery device for inserting an interbody implant into an intervertebral space in a patient has an elongate tube with a channel and is sized to fit in an intervertebral space. The elongate tube has a proximal portion, a distal portion, a longitudinal axis, and a window with a longitudinal axis. The window is disposed adjacent the distal portion of the elongate tube and the longitudinal axis of the window is offset from the longitudinal axis of the elongate tube. The channel is sized to receive the interbody implant, and also the channel is configured such that the interbody implant is advanced therealong from the proximal region toward the distal region. The interbody implant is deployed into the intervertebral space from the window.

27 Claims, 19 Drawing Sheets

(56) References Cited

U.S. PATENT DOCUMENTS

| | | |
|---|---|---|
| 2006/0265077 A1 | 11/2006 | Zwirkoski |
| 2007/0067035 A1 | 3/2007 | Falahee |
| 2007/0093828 A1* | 4/2007 | Abdou ................. A61B 17/025 606/86 A |
| 2007/0149978 A1 | 6/2007 | Shezifi et al. |
| 2008/0125865 A1 | 5/2008 | Abdelgany |
| 2008/0133012 A1 | 6/2008 | McGuckin |
| 2008/0249628 A1 | 10/2008 | Altarac et al. |
| 2009/0030423 A1* | 1/2009 | Puno ....................... A61F 2/442 606/99 |
| 2009/0143859 A1 | 6/2009 | McClellan, III et al. |
| 2009/0157186 A1 | 6/2009 | Magerl |
| 2009/0240335 A1 | 9/2009 | Arcenio et al. |
| 2011/0029085 A1 | 2/2011 | Hynes et al. |
| 2011/0046740 A1 | 2/2011 | Chen et al. |
| 2011/0264228 A1 | 10/2011 | Johnson et al. |
| 2011/0282459 A1 | 11/2011 | McClellan, III et al. |
| 2012/0016481 A1 | 1/2012 | Zwirkoski |
| 2012/0071980 A1 | 3/2012 | Purcell et al. |
| 2012/0136442 A1* | 5/2012 | Kleiner ................. A61F 2/4455 623/17.11 |
| 2012/0150302 A1 | 6/2012 | Gray |
| 2012/0158140 A1 | 6/2012 | Miller et al. |
| 2012/0158150 A1 | 6/2012 | Siegal |
| 2012/0215316 A1 | 8/2012 | Mohr et al. |
| 2012/0259416 A1 | 10/2012 | Blackwell et al. |
| 2012/0290096 A1 | 11/2012 | Messerli |

\* cited by examiner

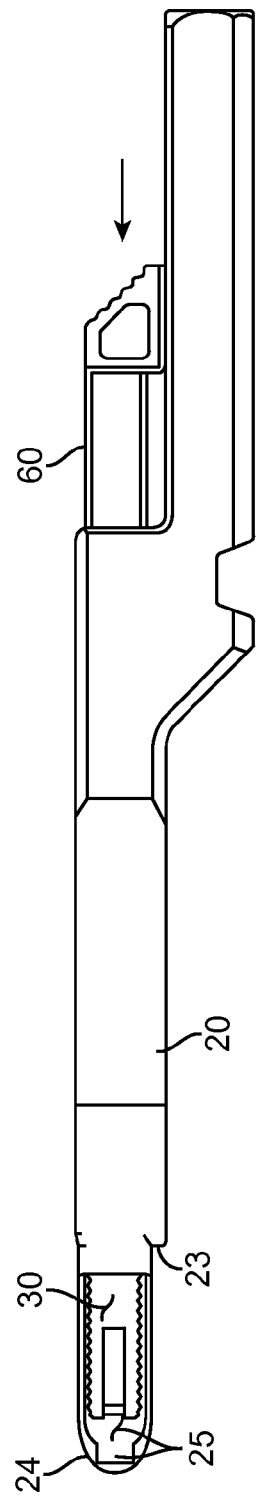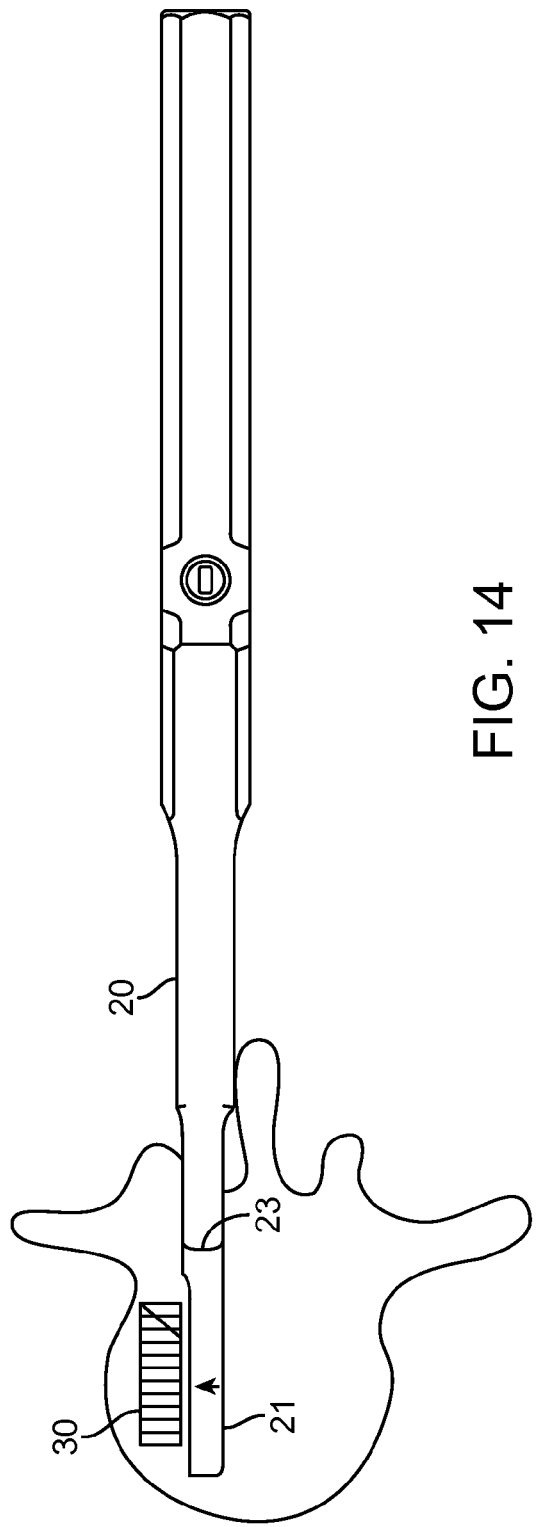

METHODS AND APPARATUS FOR IMPLANTING AN INTERBODY DEVICE

CROSS-REFERENCE

None.

The present application is related to U.S. patent application Ser. No. 13/797,586; the entire contents of which are incorporated herein by reference.

BACKGROUND OF THE INVENTION

1. Field of the Invention

The present invention generally relates to medical devices and methods. More specifically, the present invention relates to a device and method for delivering implants such as an interbody implant to a space such as an intervetebral space.

2. Background of the Invention

Whether from degenerative disease, traumatic disruption, infection or neoplastic invasion, alterations of the normal anatomical relationships between the spinal vertebrae can cause significant pain, deformity and disability. Spinal disease is a major health problem and procedures that surgically reconstruct the spinal column have become common procedures in the industrialized world.

Vertebral fusion may be accomplished by using an anterior, lateral or posterior approach and each has particular advantages and drawbacks. Frequently, circumferential fusion of the unstable level with fixation of both the anterior and posterior aspect of the spine is desired. This requires that patients undergo a combination of the aforementioned approaches. The anterior or lateral approaches are used to insert the bone graft into the disc space between the adjacent vertebrae while the posterior approach is used to place bone screws or similar fasteners that are used to immobilize the vertebral bodies. Other implants such as interbody devices may also need to be deployed.

Commercially available surgical instruments and methods of use have varying degrees of success. In some instances, the instruments have a large profile and can obstruct the surgical field, or they require excessive tissue retraction or bone decompression in order to fit in the treatment area. In other instances, the instruments and methods may not utilize the easiest pathway to the treatment area or provide adequate access. For example, in some intervertebral implantations of interbody devices, the surgeon may deliver the device laterally relative to the spinal midline thereby requiring more bone to be removed in order for the delivery device and implant to fit in the space. Bone removal is generally avoided when possible. Therefore it would be desirable to provide delivery devices and methods that permit a more medial delivery in order to reduce the amount of bone removal required. Additionally, interbody devices may have to be delivered individually thereby requiring more operating room time. Therefore, it would also be desirable if bilateral delivery of interbody implants could be performed. At least some of these objectives will be satisfied by the various embodiments disclosed in this specification.

SUMMARY OF THE INVENTION

The present invention generally relates to medical devices and methods of use. More specifically, the present invention relates to a device and method for delivering implants to a body space. While the exemplary embodiments described below are directed to delivery of an interbody implant to a space such as an intervertebral space, this is not intended to be limiting and one of skill in the art appreciates that the devices and methods described herein may be used to treat other parts of the body.

In a first aspect of the present invention, a delivery device for inserting an interbody implant into an intervertebral space in a patient comprises an elongate tube having a channel extending therethrough and having a predetermined height sized to fit in the intervertebral space. The elongate tube has a proximal portion, a distal portion, a longitudinal axis extending therebetween, and a window with a longitudinal axis. The window is disposed adjacent the distal portion, and the longitudinal axis of the window is offset from the longitudinal axis of the elongate tube. The channel is sized to receive the interbody implant, and also the channel is configured such that the interbody implant is advanced therealong from the proximal region toward the distal region. The interbody implant is deployed into the intervertebral space from the window.

The longitudinal axis of the window may be transverse relative to the longitudinal axis of the elongate tube, or the longitudinal axis of the window may be parallel to the longitudinal axis of the elongate tube. The interbody implant may be configured to be slidably advanced along the channel.

The elongate tube or the channel may have a substantially rectangular cross-section. The distal portion of the elongate tube may have a stopping element for stopping distal movement of the interbody implant therepast. The stopping element may comprise a closed distal-most end of the elongate tube. The elongate tube may also have a protuberance extending radially outward from an outer surface thereof, and the protuberance may be configured to allow insertion of the elongate tube into the intervertebral space only to a predetermined depth. The elongate tube may further comprise a coupling element for rigidly coupling the elongate tube with a second tube or another tool.

The delivery device may further comprise an elongate pusher shaft that is movably disposed in the channel. The elongate pusher shaft may be configured to engage and push the interbody implant distally along the channel, and the elongate pusher shaft may push and expel the interbody implant through the window into the intervertebral space. The elongate pusher shaft may have an angled surface relative to the longitudinal axis, and the angled surface may be adjacent a distal end of the elongate pusher shaft. The angled surface may be configured to engage the interbody implant such that a longitudinal force applied to the elongate pusher shaft is converted into a lateral force, the lateral force being normal to the angled surface, and wherein the lateral force pushes the interbody implant through the window into the intervertebral space. The elongate pusher shaft may be releasably coupled to the interbody implant so that that the interbody implant moves with the elongate pusher shaft. The pusher shaft may be slidably disposed in the channel.

The elongate tube may comprise first and second opposed surfaces that are adjacent a distal portion thereof. The opposed surfaces may be adjacent a distal portion of the elongate tube. The first and the second opposed surfaces may be biased into a collapsed configuration and they may be expandable into an expanded configuration. In the expanded configuration the first and second opposed surfaces may expand outward. The first and second opposed surfaces may comprise a plurality of fingers that may be biased into a collapsed configuration and expandable into an expanded configuration. In the expanded configuration the plurality of fingers expand radially outward and are configured to engage a superior endplate and an inferior endplate in the intervertebral space, and wherein the plurality of fingers expand into the expanded configuration when the interbody implant is engaged therewith and has a height greater than the predetermined height of the elongate tube. The plurality of fingers may be pivotably coupled to the elongate tube to allow expansion thereof. At least some of the plurality of fingers may be flexible to allow expansion thereof.

In another aspect of the present invention, a system for delivering an interbody implant into an intervertebral space comprises any of the delivery devices described herein and an interbody implant. The system may further comprise a second interbody implant. The system may also comprise an elongate pusher shaft movably disposed in the channel. The elongate pusher shaft may be configured to engage and push the interbody implant distally along the channel. The elongate pusher shaft may expel the interbody implant through the window into the intervertebral space.

In still another aspect of the present invention, a delivery device for bilateral insertion of a plurality of interbody implants into an intervertebral space in a patient comprises a first elongate tube, a second elongate tube, and a coupling element. The first elongate tube has a first channel extending therethrough and has a predetermined height sized to fit in the intervertebral space. The first elongate tube has a proximal portion, a distal portion, a longitudinal axis extending therebetween, and a first window with a longitudinal axis. The first window is disposed adjacent the distal portion, and the longitudinal axis of the first window is offset from the longitudinal axis of the first elongate tube. The first channel is sized to receive a first interbody implant, and the first channel is also configured such that the first interbody implant is advanced therealong from the proximal region toward the distal region. The first interbody implant is deployed into the intervertebral space from the first window. A first elongate pusher shaft is disposed in the first channel, and the first elongate pusher shaft is configured to engage and push the first interbody implant distally along the first channel. The first elongate pusher shaft expels the first interbody implant through the first window into the intervertebral space.

The second elongate tube has a second channel extending therethrough and has a predetermined height sized to fit in the intervertebral space. The elongate tube has a proximal portion, a distal portion, a longitudinal axis extending therebetween, and a second window having a longitudinal axis. The second window is disposed adjacent the distal portion and the longitudinal axis of the second window is offset from the longitudinal axis of the second elongate tube. The second channel is sized to receive a second interbody implant, and the second channel is configured such that the second interbody implant is advanced therealong from the proximal region toward the distal region. The second interbody implant is deployed into the intervertebral space from the second window. A second elongate pusher shaft is movably disposed in the second channel, and the second elongate pusher shaft is configured to engage and push the second interbody implant distally along the second channel. The second elongate pusher shaft expels the second interbody implant through the second window into the intervertebral space.

The coupling element is connected to the first and second elongate tubes. The connection may be adjustable or fixed. A longitudinal force applied to both of the elongate pusher shafts is converted into a first and a second lateral force that are opposed to one another and normal or transverse to the respective longitudinal axis. The lateral forces push the respective interbody implant through the respective window into the intervertebral space.

The longitudinal axis of the first or the second window may be transverse to the respective longitudinal axis of the elongate tube, or the longitudinal axis of the first or the second window may be parallel to the respective longitudinal axis. The first or the second elongate tube or the first or the second channel may have a substantially rectangular cross-section. The distal portion of the first elongate tube or the distal portion of the second elongate tube may have a stopping element for stopping distal movement of the respective interbody implant therepast. The stopping element may comprise a closed distal-most end of the respective elongate tube. The first or the second elongate tube may comprise a protuberance extending radially outward from an outer surface thereof. The protuberance is configured to allow insertion of the respective elongate tube into the intervertebral space only to a predetermined depth.

The first elongate pusher shaft or the second elongate pusher shaft may comprise an angled surface relative to the respective longitudinal axis and that is adjacent a distal end of the respective elongate pusher shaft. The angled surface may be configured to engage the respective interbody implant such that a longitudinal force applied to the respective elongate pusher shaft is converted into a lateral force. The lateral force is preferably normal to the angled surface such that the lateral force pushes the respective interbody implant through the respective window into the intervertebral space. The first elongate pusher shaft or the second elongate pusher shaft may be releasably coupled to the respective interbody implant so that the respective interbody implant moves with the respective elongate pusher shaft. The first elongate pusher shaft may be coupled to the second elongate pusher shaft such that the first and second elongate pusher shafts move together in their respective channel.

In another aspect of the present invention, a system for bilateral delivery of a plurality of interbody implants to an intervertebral space comprises any of the delivery devices described herein and also comprises the first interbody implant and the second interbody implant. The system may further comprise a third interbody implant.

In still another aspect of the present invention, a method for delivering an interbody implant into an intervertebral space in a patient comprises providing a delivery device, postioning the delivery device, moving an implant along the delivery device, and passing the implant through a window in the delivery device. The delivery device has an elongate tube with a channel disposed therein and an interbody implant disposed in the channel. The distal portion of the elongate tube is positioned into the intervertebral space, and the interbody implant is moved distally along the channel. The interbody implant is then passed laterally through a window adjacent the distal portion of the elongate tube into the intervertebral space.

Moving the interbody implant may comprise pushing the interbody implant with an elongate pusher shaft slidably disposed in the channel. Passing the interbody implant through the window may comprise laterally expelling the interbody implant through the window relative to a longitudinal axis of the delivery device. Passing the interbody implant through the window may comprise radially expanding upper and lower opposed surfaces disposed adjacent the distal portion of the elongate tube and passing the interbody implant therethrough. The delivery device may comprise a second elongate tube with a second channel disposed therein and a second interbody implant disposed in the second channel. The method may further comprise positioning a distal portion of the second elongate tube into the intervertebral space, moving the interbody implant distally along the second channel, and passing the second interbody implant through a second window adjacent the distal portion of the second elongate tube into the intervertebral space. The first and second interbody implants may be passed through their respective windows simultaneously. The method may further comprise limiting the advancement of the distal portion of either elongate tube into the intervertebral space with a protuberance extending radially outward from an outer surface of the respective elongate tube. Passing the second interbody implant may comprise laterally ejecting the second interbody implant from the second window. The interbody implant may comprise a plurality of interbody implants.

These and other aspects and advantages of the invention are evident in the description which follows and in the accompanying drawings.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 13 is an elevation view of the insertion tube, with the shaft and implant inserted within the insertion tube;

FIG. 14 is a top plan view of the insertion tube of FIG. 7 showing an implant deployed lateral to the insertion tube;

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Figure 1:
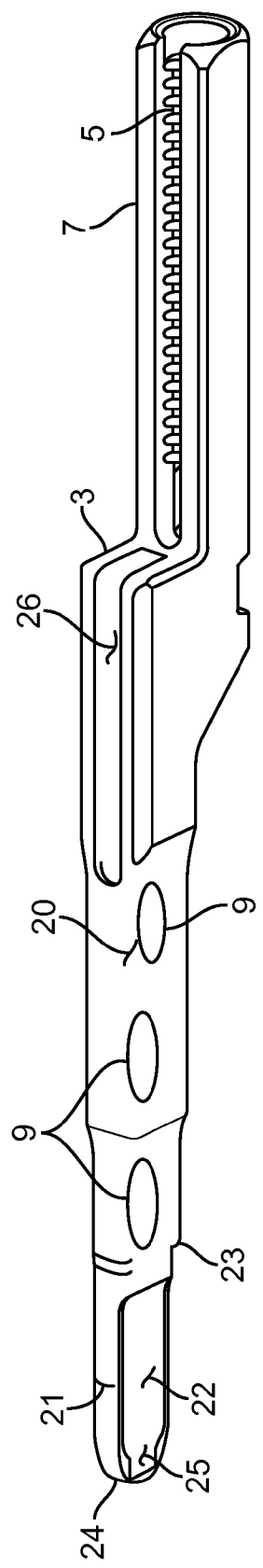
FIG. 1 is a perspective view illustrating a spinal implant insertion tube.
Figure 4:
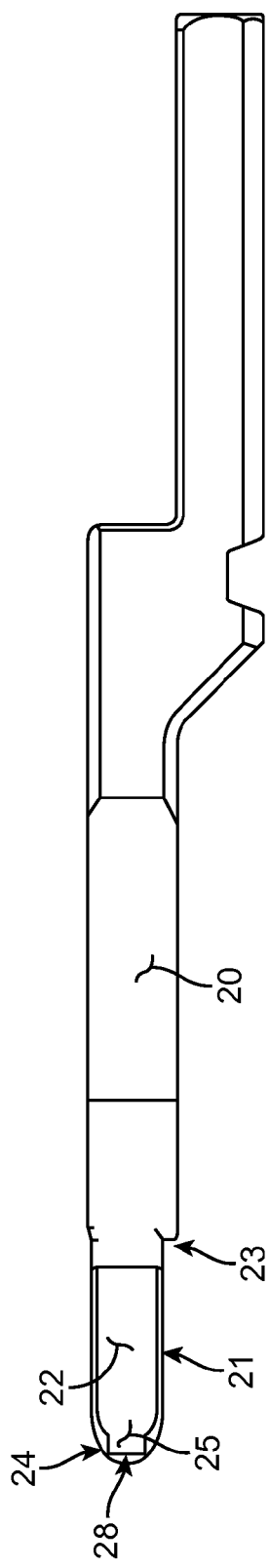
FIG. 4 is an elevation view of an insertion tube.
Figure 4A:
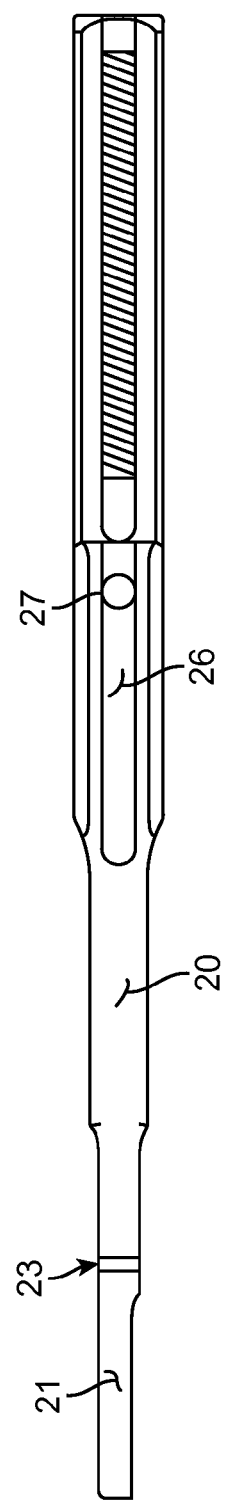
FIG. 4A is a top plan view of the insertion tube in FIG. 4.
Figure 6:
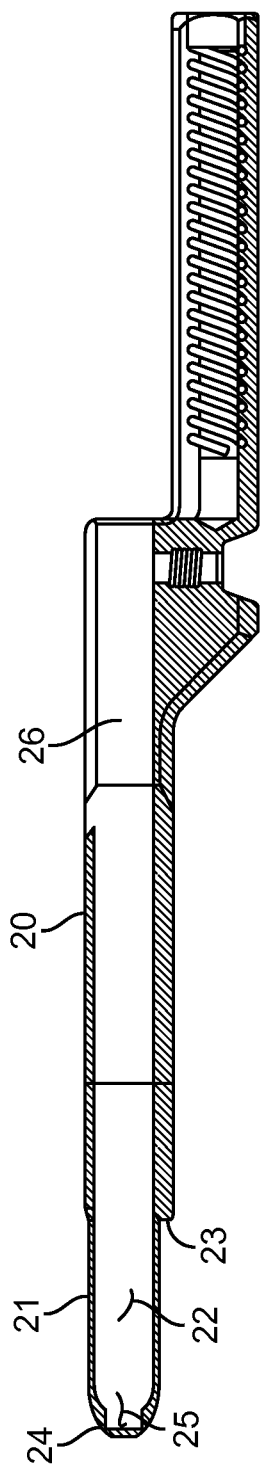
FIG. 6 is a cross-sectional view of the insertion tube in FIG. 4.

FIG. 1 shows the insertion tube 20 with slot 26 for insertion of an intervertebral implant and insertion shaft. The slot 26 (also referred to as a channel) extends along the insertion tube 20 toward the distal end 21. The distal end of the insertion tube 21 includes a rounded atraumatic distal tip 24 for ease of insertion into the disk space, a stepped region forms a protuberance 23 which serves as a mechanical stop to prevent insertion of the tube 20 past the desired placement in the disc space and window 22, which allows for deployment of the intervertebral implant. Additional relief 25 in window 22 and/or distal end of the insertion tube 20 provides clearance for the distal end of the insertion shaft during deployment of the intervertebral implant. In alternative embodiments, the distal end 21 may have an opening that provides the clearance. The window has a longitudinal axis that preferably is laterally offset from the longitudinal axis of the insertion tube 20. Thus, the longitudinal axis of the window in preferred embodiments is parallel to the longitudinal axis of the insertion tube 20, but not coaxial therewith. In alternative embodiments, the window may be angled transversely to the longitudinal axis of the insertion tube 20. The insertion tube 20 also includes a handle 7 that allows a surgeon to easily hold and manipulate the device. An optional threaded portion 5 in the handle allows a pusher shaft (not illustrated here) to be threadably actuated so that it moves along the slot 26. Optional through holes 9 extending from the outer surface of the insertion tube and communicating with the slot 26 may be disposed in the sidewalls of the insertion 20. The through holes 9 help lighten the device which may be fabricated from metals such as stainless steel or polymers such as ABS, PVC, or other polymers used for surgical instruments. Additionally, the through holes 9 allow the device to be more easily cleaned and sterilized if the device is reusable and resterilizable. The device may be single use. The slotted region 26 is offset from the longitudinal axis of the handle 7 thereby forming a shoulder 3 which acts as a stop to prevent over insertion of the pusher shaft as discussed below. Additionally, the offset allows a surgeon to look down the slot to view the surgical field. FIGS. 4 and 4A illustrate alternative views of the insertion tube. Hole 27 (best seen in FIG. 4A) allows a fastener such as a screw to coupled to the insertion tube. This allows other instruments such as a second insertion tube to be coulpled to the first insertion tube. FIG. 6 illustrates yet another alternative view of the insertion tube 20.

Figure 2:
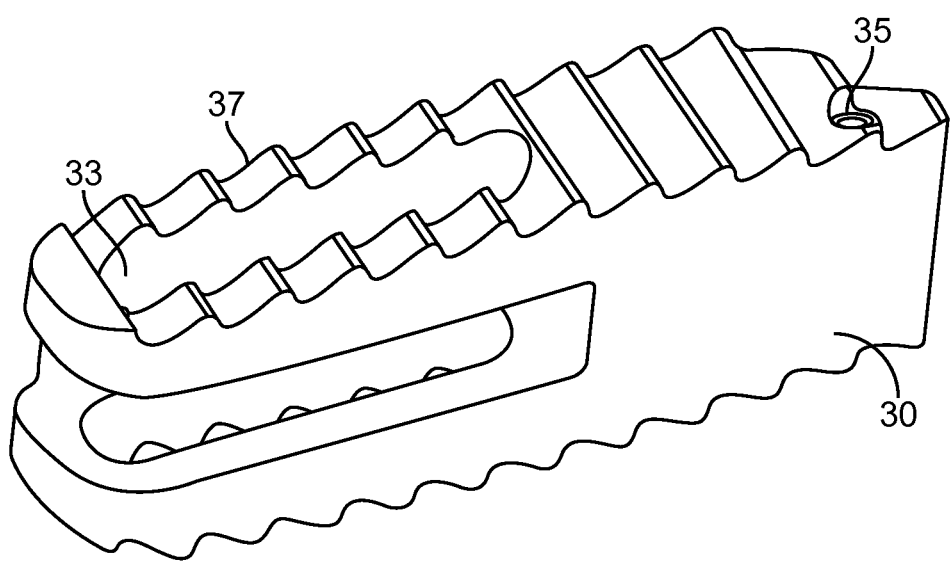
FIG. 2 is a perspective view of a spinal implant to be inserted.
Figure 2A:
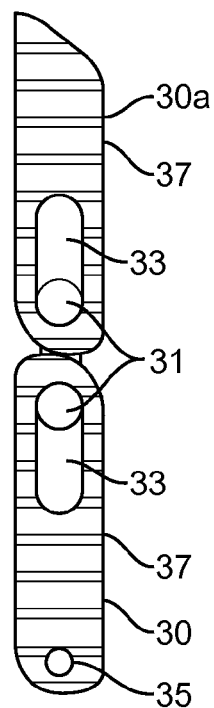
FIGS. 2A-2C are a top view of a plurality of spinal implants.
Figure 2B:
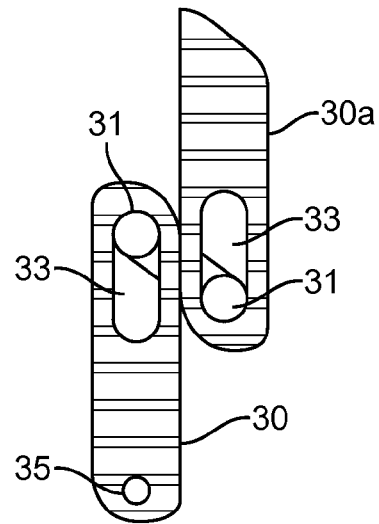
Figure 2C:
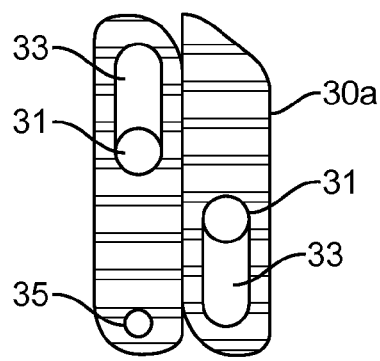

FIG. 2 is an illustration of an exemplary interbody implant 30 that may be used as an intervertebral implant, often during spinal fusion. The implant 30 includes a textured surface 37 on the superior and inferior surfaces of the implant that help grip and keep the implant in position between vertebral endplates. An aperture 35 on one end of the implant allows a radiopaque marker such as a metal pin to be inserted therein to facilitate visualization under x-ray or other fluoroscopic imaging techniques. A slotted region 33 allows the implant to be coupled with a second implant. In certain circumstances, it may be advantageous to couple two implants together such as in FIG. 2A where implant 30 is coupled with a second implant 30a. The two implants may be identical to one another or different. Additional information related to the implants and their use is disclosed in U.S. patent application Ser. No. 13/797,586; the entire contents of which is incorporated herein by reference. A pin 31 is used to couple the two implants together and the pin 31 allows the implants to move relative to one another as seen in FIGS. 2B and 2C where the implants move from a serial configuration to a parallel configuration. This provides a lower profile for delivery and a larger support area once implanted.

Figure 3:
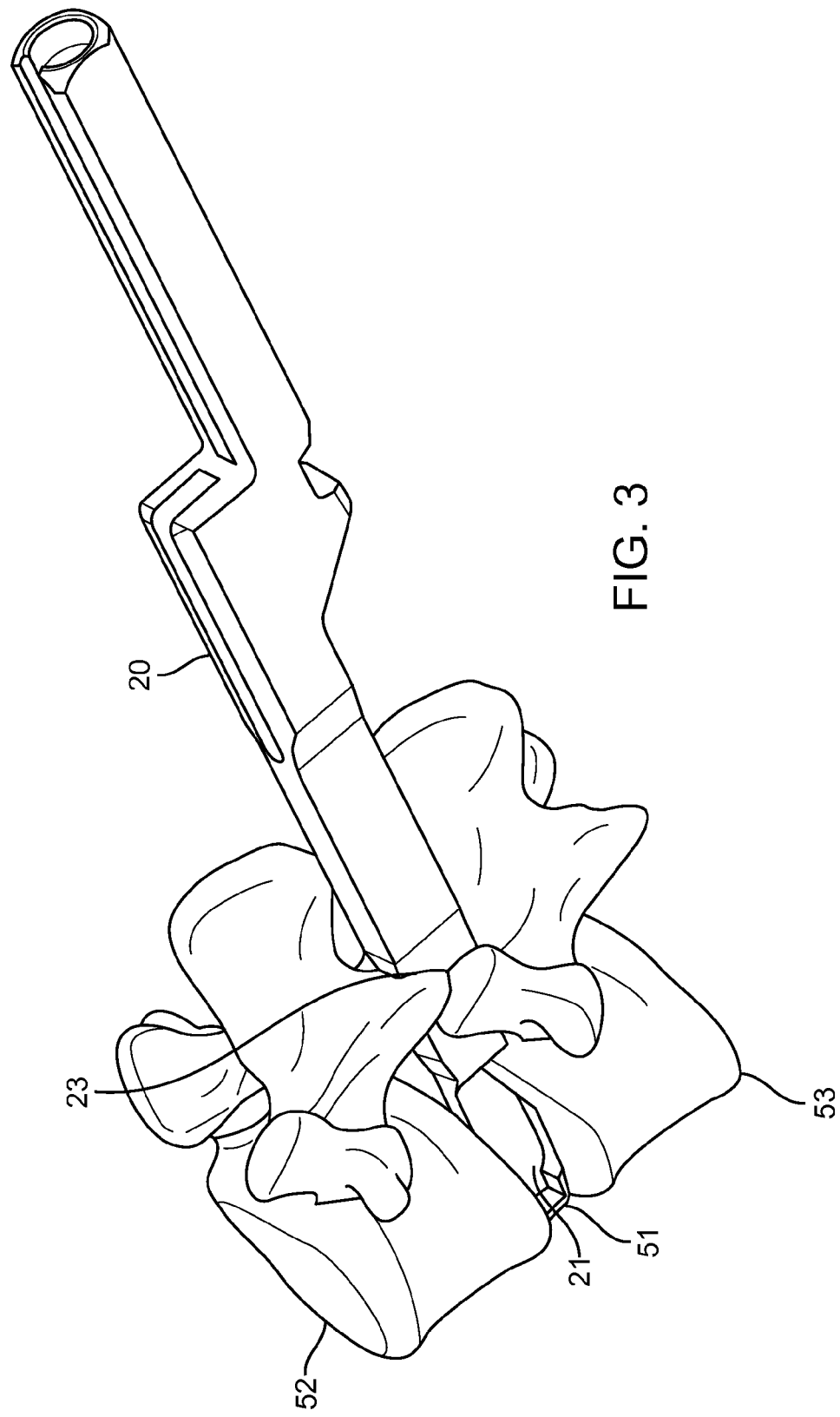
FIG. 3 is a perspective view illustrating one insertion tube placed in the intervertebral space.

FIG. 3 shows the distal end 21 of insertion tube 20 fully inserted into the intervertebral disc space, 51 between the superior adjacent vertebra 52 and the inferior adjacent vertebra 53. Further insertion of insertion tube 20 is prohibited because the stepped region 23 abuts against the bone, thereby providing a mechanical stop.

Figure 5:
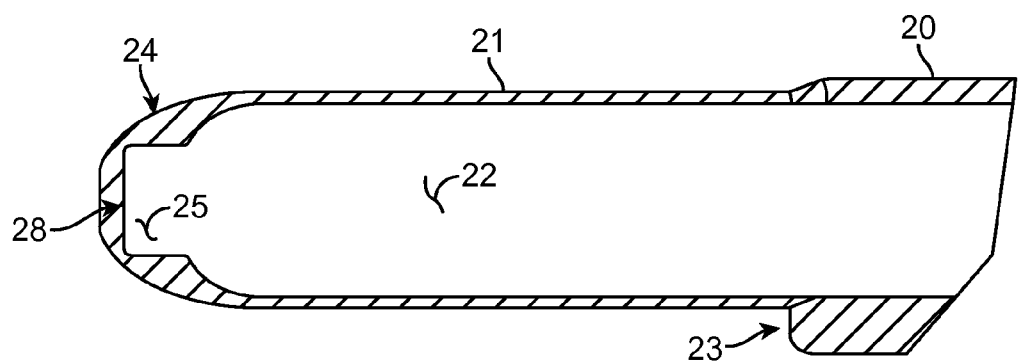
FIG. 5 is a cross-sectional elevation view of the distal end of the insertion tube illustrated in FIG. 4.
Figure 5A:
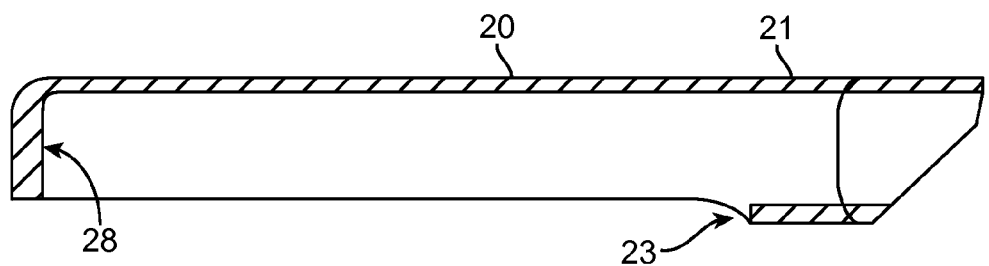
FIG. 5A is a cross-sectional top view of the distal end of the insertion tube illustrated in FIG. 4A.

FIG. 5 is a cross-sectional view of the distal end 21 of insertion tube 20, showing the closed end 28 of the insertion tube, which prevents expulsion of the intervertebral implant along the axis of the tube, thereby enabling deployment through window 22. Additionally, receptacle 35 provides a recessed region for receiving the distal end of the pusher shaft. The closed end prevents the pusher shaft from extending past the distal end of the insertion tube thereby preventing any sharp points from protruding from the insertion tube 20. The recessed region also accommodates the distal portion of the pusher shaft which may have a coupling mechanism for coupling with the implant. By accommodating the coupling mechanism, the pusher shaft does not have to be moved further distally to account for the length of the coupling mechanism, and the window similarly may be positioned more proximally along the insertion tube. In alternative embodiments, instead of a receptacle, a small aperture may be disposed in the distal end of the insertion tube to accommodate a coupling mechanism or the distal portion of the pusher shaft. FIG. 5A illustrates an alternative view of FIG. 5.

Figure 7:
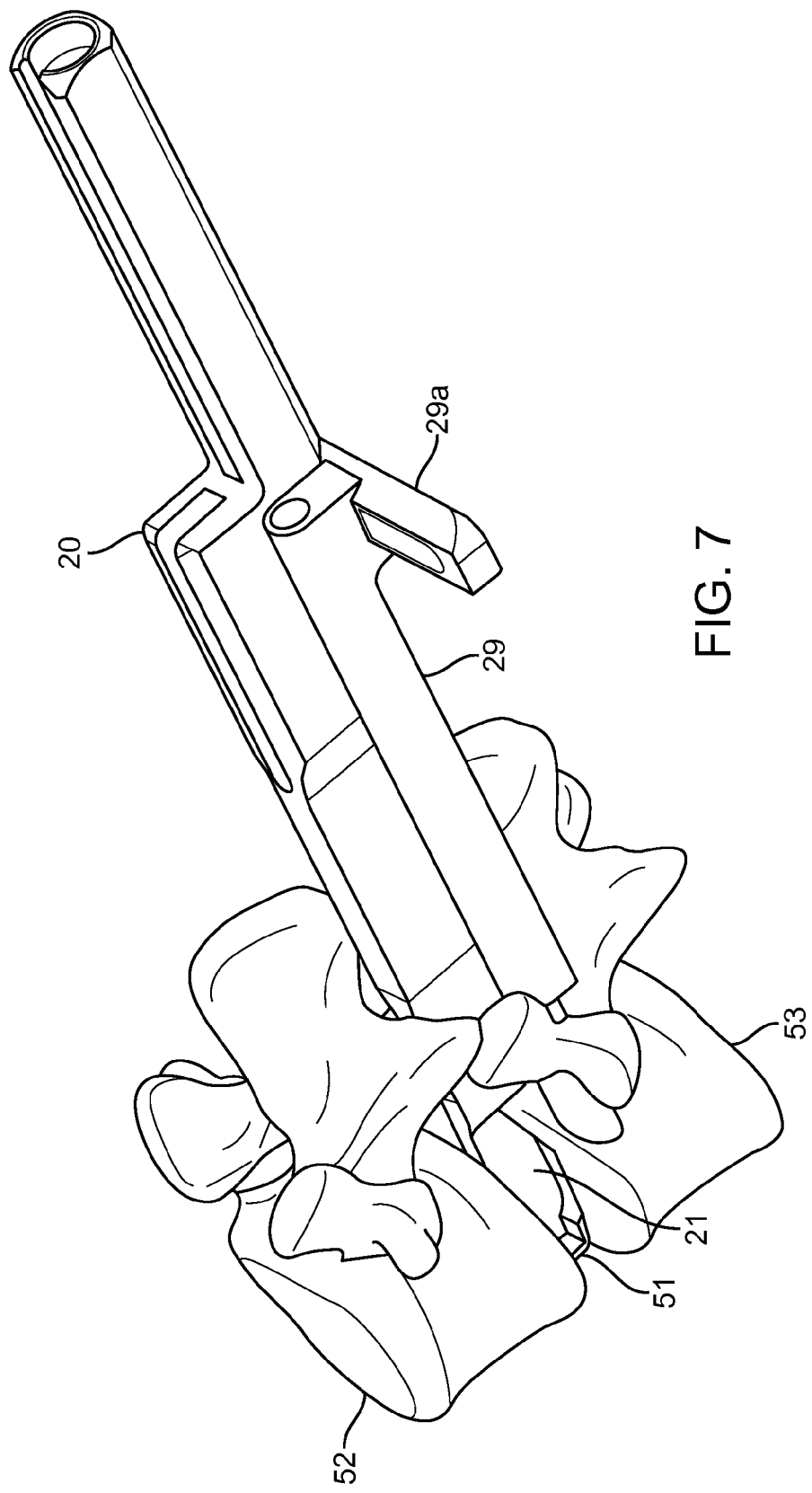
FIG. 7 is a perspective view of the insertion tube of the present invention placed in and the intervertebral space and anchored to the pedicle of the adjacent vertebral body.

FIG. 7 shows supplemental fixation of tube 20 by attaching pedicle anchor 29 to tube 20 and securing anchor 29 directly to the pedicle of the inferior adjacent vertebra 53. The pedicle anchor 29 may comprise a tube that is coupled to a coupling member 29a which is fixedly or releasably attached to insertion tube 20. The tube 29 may be slidably adjustable along coupling member 29a to adjust the lateral distance between the tube 29 and the insertion tube 20. The tube 29 has a channel extending through it and is sized to receive an elongate screw which is threadably engaged with the pedicle or any portion of the vertebrae, thereby rigidly supporting and helping to stabilize the insertion tube.

Figure 8:
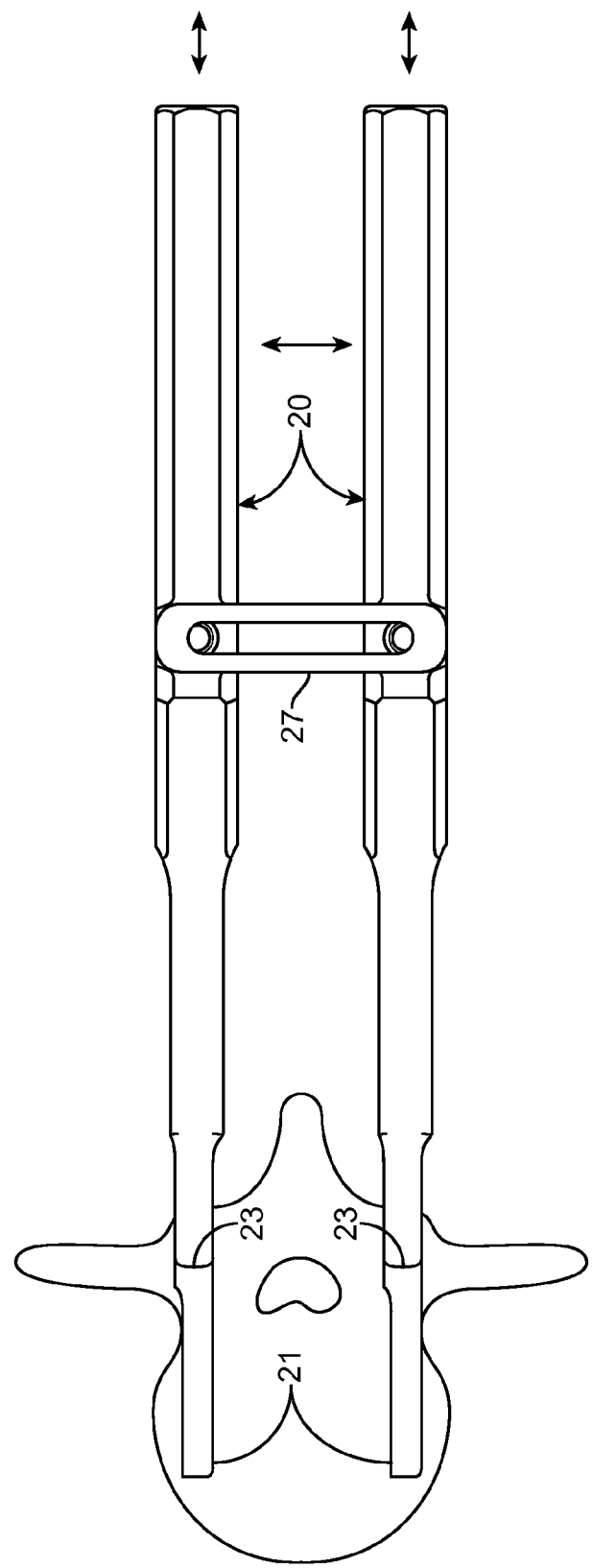
FIG. 8 is a top plan view of bilateral insertion tubes of the present invention placed in the intra-vertebral space and coupled to each other by a connecting member.
Figure 9:
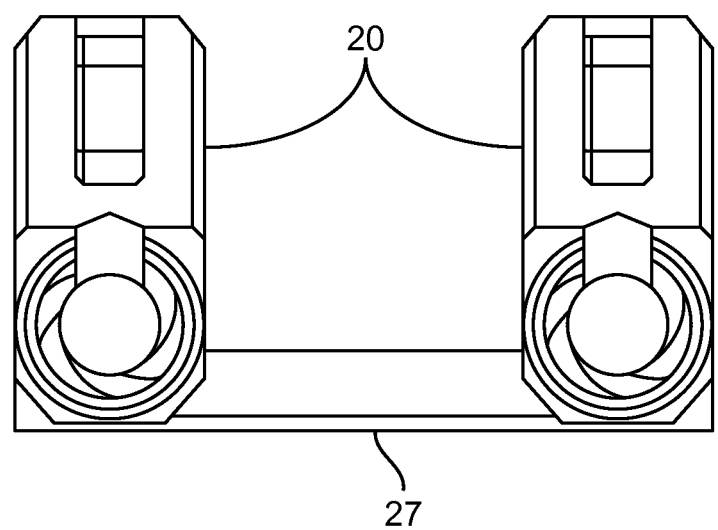
FIG. 9 is an end elevation view of the insertion tubes and connecting member in FIG. 8.

FIG. 8 illustrates a bilateral use of two tubes 20, rigidly coupled for stability by connecting member 27. A connector element 27 may be fixedly or releasably attached to the two insertion tubes 20 to rigidly connect them together as previously described in FIG. 7 above. The connector element 27 may be slotted in order to allow adjustment of the two tubes 20 relative to one another; either axially, laterally, or both, as indicated by the arrows in FIG. 8. FIG. 9 illustrates an alternative view of FIG. 8.

Figure 10:
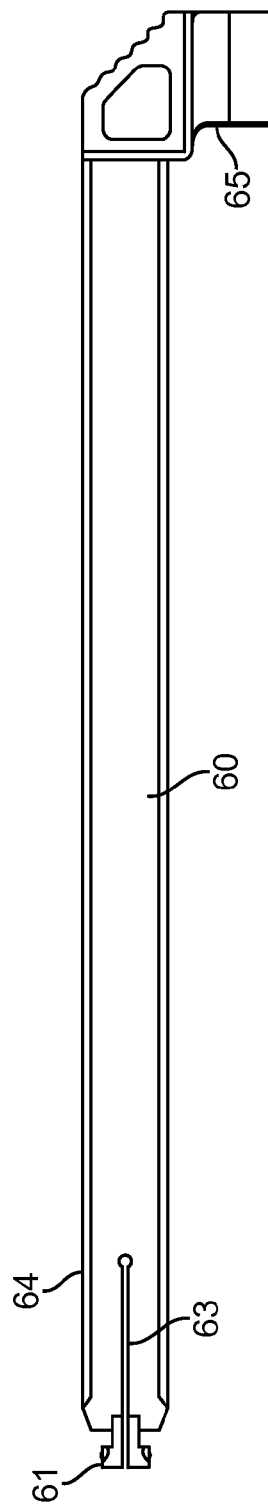
FIG. 10 is an elevation view of the insertion shaft.
Figure 10A:
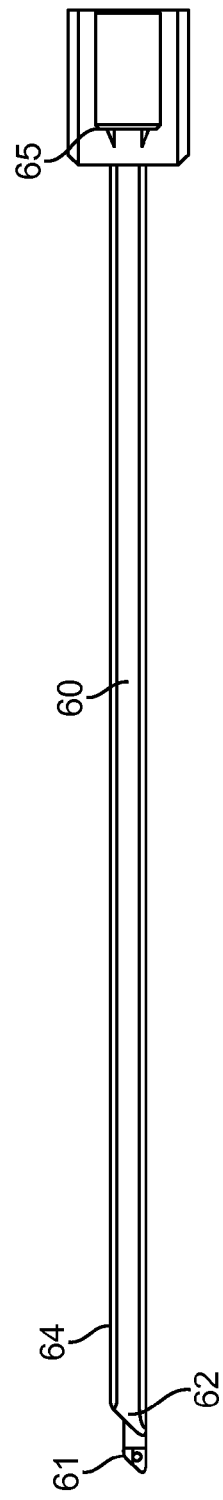
FIG. 10A is a top plan view of the insertion shaft.

FIG. 10 shows the insertion shaft 60 (also referred to herein as a pusher shaft), which is used to insert and deploy the intervertebral implant 30. The insertion shaft is optional, as the implant may be advanced along the insertion tube by other means. The implant attachment connector 61 is flexibly formed on the distal end 64 of the shaft 60, such that when assembled to the intervertebral implant 30, the connector 61 collapses slot 63 sufficiently to connect or disconnect from implant 30 by applying force along the long axis of the shaft 60. In this embodiment, the attachment connector or coupling mechanism 61 is a T-shaped connector element having a base with two arms extending therefrom and forming the T. The arms may be received in a cooperating receptacle on the implant so that the implant is releasably coupled therewith. The proximal end of the shaft (not numbered) is adapted for applying force to the shaft by a variety of methods, including hand pressure, mallet or screw thread. Additionally, the proximal end of the pusher shaft has a portion 65 which extends radially outward. This portion will abut against stop 3 (seen in FIG. 1) to prevent the pusher shaft from being advanced too far. FIG. 10A further illustrates the angled surface 62 at the distal end 64 of the shaft 60. Angled surface 62 applies a lateral force to implant 30 when the implant reaches the distal end of tube 20 and force is applied to shaft 60. The lateral force pushes the implant out the window of the insertion tube.

Figure 11:
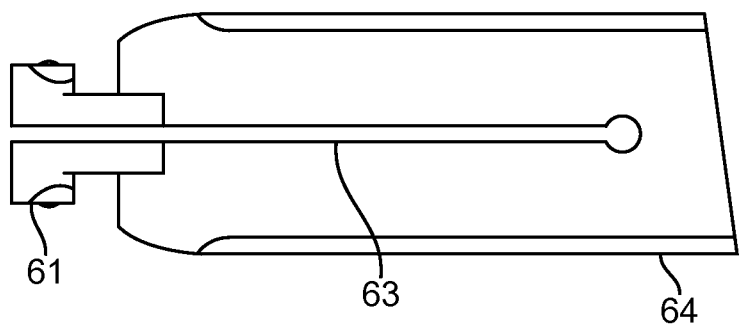
FIG. 11 is a cross-sectional elevation view of the distal end of the insertion shaft in FIG. 10.
Figure 11A:
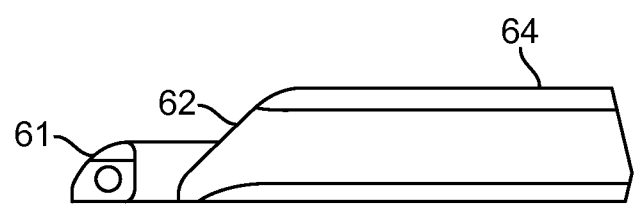
FIG. 11A is a cross-sectional top view of the distal end of the insertion shaft in FIG. 10A.

FIG. 11 and FIG. 11A are enlarged views of the distal end 64 of shaft 60.

Figure 12:
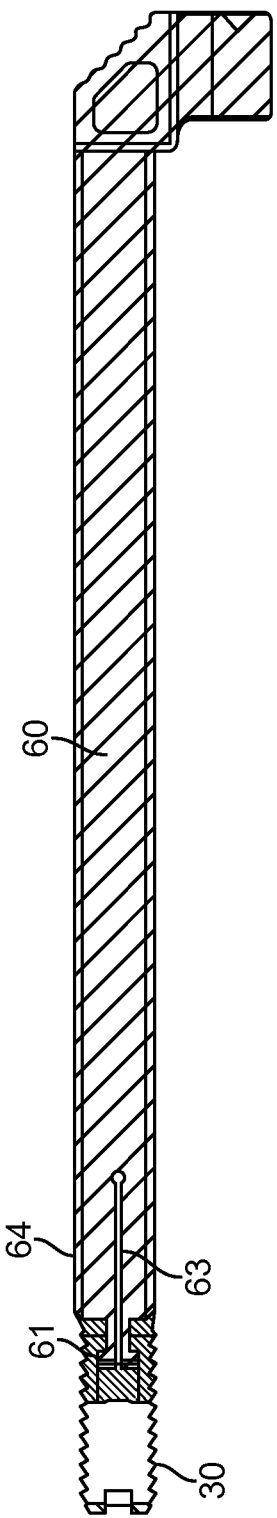
FIG. 12 is an elevation view of the insertion shaft in FIG. 10 coupled to an implant.
Figure 12A:
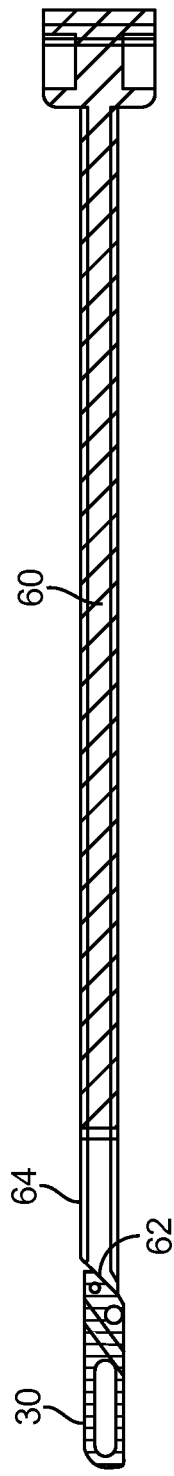
FIG. 12A is a top plan view of the insertion shaft in FIG. 10 coupled to an implant.

FIG. 12 and FIG. 12A show implant 30 assembled on shaft 60. FIG. 12 shows the T-shaped connector element 61 releasably coupled to a receptacle in the implant 30. As the pusher shaft advances the implant along the channel in the insertion tube, it will exert a lateral force on the implant and eject the implant from the window. This force also decouples the T-shaped connector element 61 from the implant and releases the implant so that it may be delivered to the treatment site.

FIG. 13 illustrates implant 30, assembled on shaft 60, inserted into tube 20 as implant 30 approaches the distal end 21 of tube 30, just prior to deployment of implant 30 from tube 20. As the pusher shaft 60 is further advanced distally, the implant will be pushed out the window in the insertion tube. FIG. 14 shows the lateral position of a fully deployed implant 30, with tube 20 still in place in the intervertebral space.

Figure 15:
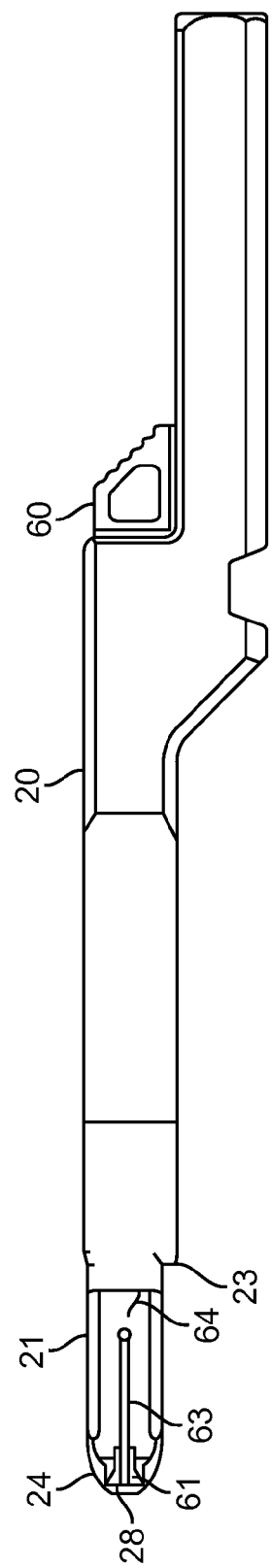
FIG. 15 is an elevation view of the shaft fully inserted into the insertion tube after deployment of the implant (implant not shown for clarity)

FIG. 15 illustrates the position of the distal end 64 of shaft 60 in the distal end 21 of tube 20 when implant 30 (not shown) is fully deployed. The implant attachment connector 61 can be seen in the relief area 25 (see FIG. 5) of window 22 (see FIG. 5). This relief allows full insertion of distal end 64 of shaft 60, thereby providing full lateral deployment of implant 30.

Figure 16:
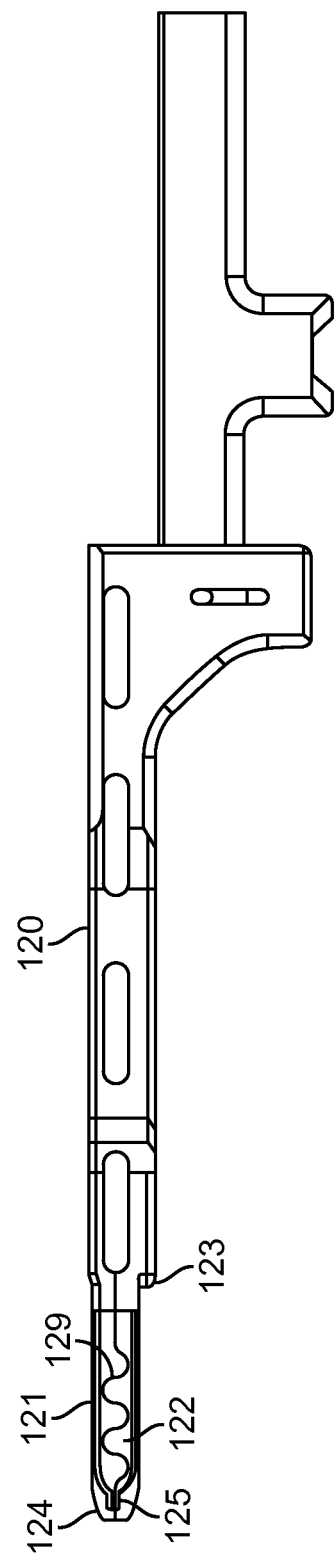
FIG. 16 is an elevation view of an alternate embodiment of an insertion tube.

FIG. 16 shows an alternate embodiment 120 of the insertion tube. This embodiment generally takes the same form as the previous embodiment with the main difference being the expandable insertion tube that accommodates implants with greater height. The distal end 121 of tube 120 includes a rounded distal tip 124, window 122, relief area 125 and insertion stop 123. The expandable insertion tube is formed from two half tubes or otherwise opposable surfaces which expand away from one another.

Figure 17:
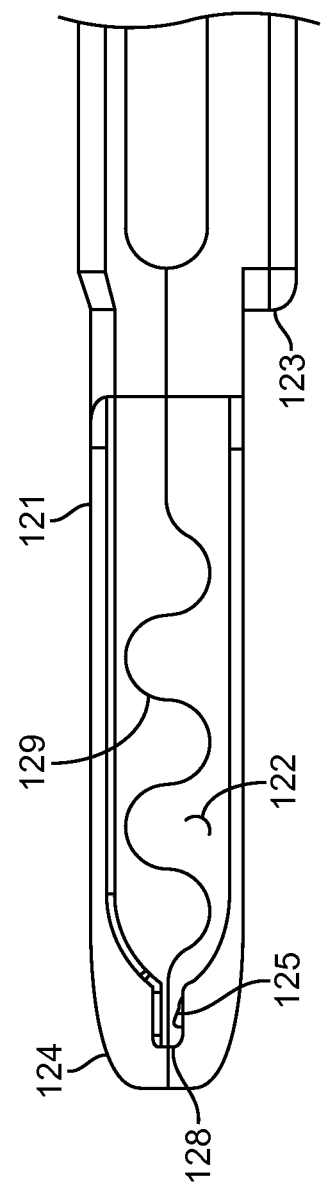
FIG. 17 is a cross-sectional view of the distal end of the insertion tube in FIG. 16.
Figure 18:
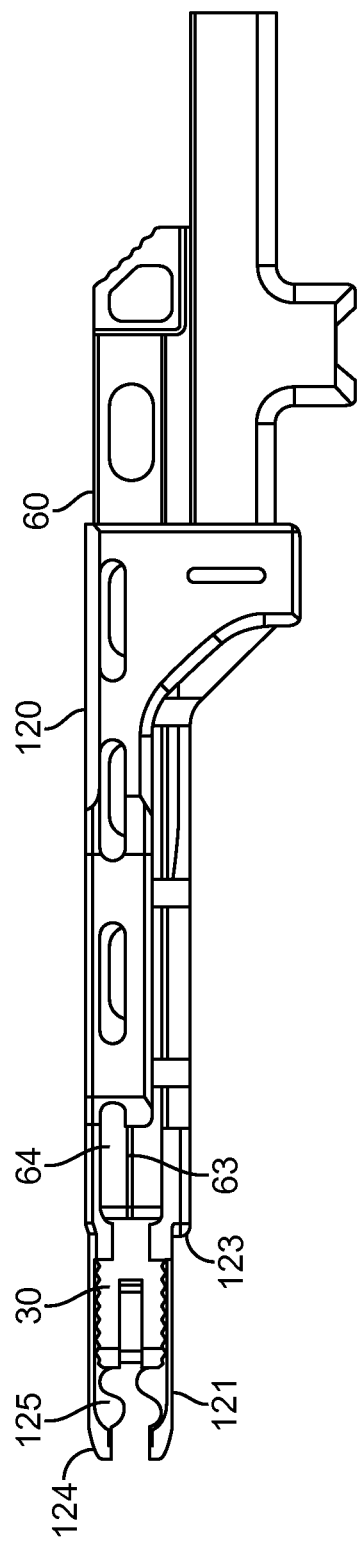
FIG. 18 is a cross-sectional view of the insertion tube in FIG. 16 showing it expanded as the implant is inserted into the distal end of the insertion tube.

FIG. 17 is an enlarged view of distal end 121, which has an upper surface and a lower surface which are opposed surfaces that are split and can spread apart. The splitting 129 of distal end 121 is highlighted in FIG. 17. The split distal end 121 provides flexibility, such that an implant 30 of height greater than the height of the split distal end 121 may be implanted into a disc space of height less than that of the implant, by insertion of distal end 121 in a closed position and expansion of distal end 121 during implantation. FIG. 18 illustrates expansion of distal end 121 of tube 120 by insertion of implant 30. In alternative embodiments, the upper and lower surfaces of the insertion tube may form a plurality of fingers which pivotably or resiliently spread apart.

Figure 19:
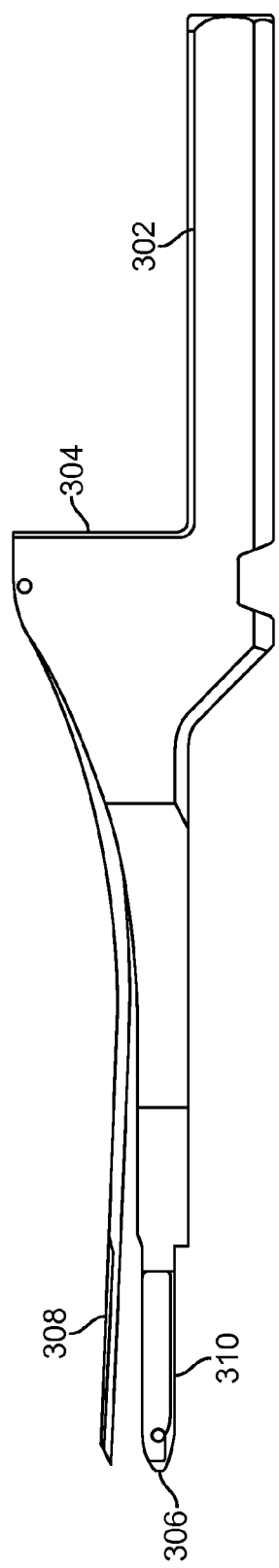
FIG. 19 is a side view of another exemplary embodiment of an insertion tube.

FIG. 19 illustrates another exemplary embodiment of an insertion tube that is generally similar to previous embodiments. The insertion tube includes a handle 302, an insertion slot 304 for receiving the implant and a rounded atraumatic distal tip 306. The distal portion of the insertion tube has an upper surface 308 and a lower surface 310 that can separate away from one another as the implant is advanced through a channel in the insertion tube. The upper and lower opposable surfaces may be pivotably coupled together as seen in FIG. 19, or the opposable surfaces may be resilient and deflect away from one another.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A delivery system for inserting an interbody implant into an intervertebral disc space, comprising:
   an interconnecting member comprising a first segment and a second segment;
   a first delivery device comprising:
      a first elongate member having a proximal portion, a distal portion, a longitudinal axis extending therebetween, and a channel extending therethrough, the channel being sized to receive at least a segment of a first interbody implant therein, the distal portion of the first delivery device being sized to fit within the intervertebral disc space and comprising a side window therein, a distal segment of the channel comprising a first element that is attached to the distal portion such that a position of the first element is fixed relative to a position of the distal portion and the proximal portion throughout implant delivery and removal of the first delivery device from the intervertebral disc space, the first element being configured to: (i) limit movement of the first interbody implant therepast throughout implant delivery, and (ii) engage the first interbody implant such that a force applied to the first interbody implant along the direction of the longitudinal axis is at least partially directed into a lateral force that advances the first interbody implant through the side window and into the intervertebral disc space;
      a first coupling element of the first elongate member configured to couple to the interconnecting member; and
      a first elongate pusher configured to engage and advance the first interbody implant at least partially through the channel;
   a second device comprising a second elongate member having a first and a second portion, the first portion comprising a second coupling element configured to couple to the interconnecting member; and
   wherein the interconnecting member is configured to couple at the first segment to the first coupling element and to couple at the second segment to the second coupling element.

2. The delivery system of claim 1, wherein the second portion of the second device is coupled to a bone fastener that is configured to be affixed onto a vertebral bone.

3. The delivery system of claim 2, wherein the coupling of the interconnecting member onto each of the first coupling element and the second coupling element is configured to stabilize the first delivery device relative to the intervertebral disc space.

4. The delivery system of claim 1, wherein the second portion of the second device is configured to deliver a second interbody implant into the intervertebral disc space.

5. The delivery system of claim 4, wherein the second device comprises the second elongate member that extends from the first portion to the second portion along a longitudinal axis and has a channel extending therethrough, the channel being sized to receive at least a segment of the second interbody implant therein.

6. The delivery system of claim 5, wherein the second portion of the second delivery device is sized to fit within the intervertebral disc space and comprises a side window therein.

7. The delivery system of claim 6, wherein the second device further comprises a second elongate pusher that is configured to engage and advance the second interbody implant at least partially through the channel of the second elongate member.

8. The delivery system of claim 7, wherein the second elongate member further comprises a second element that limits movement of the second interbody implant therepast, the second element configured to engage the second interbody implant such that a force applied to the latter along the direction of the channel of the second device is at least partially directed into a lateral force that advances the second interbody implant through the side window of the second delivery device.

9. The delivery system of claim 8, wherein the second element comprises a closed distal-most end of the second elongate member of the second device.

10. The delivery system of claim 6, wherein a longitudinal axis of the side window of the second delivery device is non-parallel to the longitudinal axis of the second elongate member of the second device.

11. The delivery system of claim 6, wherein a longitudinal axis of the side window of the second delivery device is parallel to the longitudinal axis of the second elongate member of the second device.

12. The delivery system of claim 6, wherein at least one of the first elongate member of the first delivery device or the second elongate member of the second device comprises a protuberance extending radially outward from an outer surface thereof, the protuberance configured to limit insertion of the at least one of the first or the second elongate member into the intervertebral space to a predetermined depth.

13. The delivery system of claim 6, wherein the second elongate member of the second device comprises a first and second opposed surfaces having a collapsed configuration and an expanded configuration, and
wherein, in the expanded configuration, the first and second opposed surfaces move away from one another so as to enlarge a distal aspect of the channel of the second device.

14. The delivery system of claim 1, wherein a longitudinal axis of the side window of the first delivery device is non-parallel to the longitudinal axis of the elongate member of the first delivery device.

15. The delivery system of claim 1, wherein a longitudinal axis of the side window of the first delivery device is parallel to the longitudinal axis of the first elongate member of the first delivery device.

16. The delivery system of claim 1, wherein the first interbody implant is configured to be slidably advanced along the channel.

17. The delivery system of claim 1, wherein the first element comprises a closed distal-most end of the first elongate member of the first delivery device.

18. The delivery system of claim 1, wherein the first elongate member comprises first and second opposed surfaces having a collapsed configuration and an expanded configuration, and
wherein, in the expanded configuration, the first and second opposed surfaces move away from one another so as to enlarge a distal aspect of the channel of the first delivery device.

19. The delivery system of claim 1, wherein the interconnecting member is configured to immobilize the first delivery device relative to the second device in one of a plurality of distances between the first segment and the second segment of the interconnecting member.

20. A delivery system for inserting an interbody implant into an intervertebral disc space, the delivery system comprising:
an interconnecting member comprising a first segment and a second segment;
a first delivery device comprising:
a first elongate member having a first proximal portion, a first distal portion, a first longitudinal axis extending therebetween, and a first channel extending therethrough, the first channel being sized to receive at least a segment of a first interbody implant therein, the first distal portion of the first delivery device being sized to fit within the intervertebral disc space and comprising a first side window therein, a distal segment of the channel comprising an element that limits movement of the first interbody implant therepast, the element configured to engage the first interbody implant such that a force applied to the first interbody implant along the direction of the first longitudinal axis is at least partially directed into a lateral force that advances the first interbody implant through the first side window and into the intervertebral disc space;
a first coupling element of the first elongate member configured to couple to the interconnecting member; and
a first elongate pusher configured to engage and advance the first interbody implant at least partially through the first channel; and
a second delivery device comprising:
a second elongate member having a second proximal portion and a second distal portion, the second distal portion of the second delivery device being sized to fit within the intervertebral disc space and comprising a second side window therein;
wherein the interconnecting member is configured to couple at the first segment to the first coupling element and to couple at the second segment to the second elongated member of the second device to put the delivery system into an assembled position; and
wherein, in the assembled position, a first plane of the first side window is non-coextensive with a second plane of the second side window.

21. The delivery system of claim 20, wherein the second elongate member of the second device is configured to deliver a second interbody implant into the intervertebral disc space; and
wherein the second elongate member further comprises a second longitudinal axis extending between the second proximal portion and the second distal portion and a second channel extending therethrough, the second channel being sized to receive at least a segment of the second interbody implant therein.

22. The delivery system of claim 20, wherein the second device further comprises a second elongate pusher that is configured to engage and advance the second interbody implant at least partially through the second channel of the second device.

23. The delivery system of claim 20, wherein, in the assembled position, the first plane of the first window is parallel to the second plane of the second window.

24. The delivery system of claim 20, wherein the element is further configured to engage the first interbody implant such that the force applied to the first interbody implant along the direction of the first longitudinal axis is at least partially directed into the lateral force that advances the first interbody implant through the first side window and into the intervertebral disc space toward the second device.

25. A delivery system for placement of an implant into a skeletal system of a subject, the delivery system comprising:
a non-implantable delivery device comprising:
an elongate member having a proximal portion, a distal portion and an internal channel extending therebetween, the internal channel configured to extend along a longitudinal axis and being sized to receive at least a segment of the implant therein;
a side window disposed in a distal segment of the internal channel, the side window comprising a lateral axis that is offset from, and parallel to the longitudinal axis of the internal channel;
an element of the distal segment of the internal channel, the element configured to limit the distal movement of the implant therepast and to engage the implant such that a force applied to the implant along the direction of the longitudinal axis of the internal channel is at least partially converted into a lateral force that advances the implant through the side window and expels the implant from the internal channel;

an elongate pusher configured to be at least partially seated within the internal channel and to advance the implant through the internal channel; and wherein the element is integrally formed with the distal segment such that a position of the element is fixed relative to a position of a side wall of the distal segment, the element thereby configured to be immobilized throughout implant delivery and subsequent removal of the non-implantable delivery device from the skeletal system.

26. The delivery system of claim 25, wherein the element and the elongate pusher are further configured to expel a totality of the implant from the internal channel through the side window in a lateral direction.

27. The delivery system of claim 25, wherein a height of the implant is configured to be maintained after removal of the non-implantable delivery device.

* * * * *